United States Patent [19]
Campbell

[11] Patent Number: 5,208,619
[45] Date of Patent: May 4, 1993

[54] AUTOMATIC REFRACTOR, LENSMETER AND KERATOMETER UTILIZING BADAL OPTICS

[75] Inventor: Charles E. Campbell, Berkeley, Calif.

[73] Assignee: Allergan Humphrey, San Leandro, Calif.

[21] Appl. No.: 732,268

[22] Filed: Jul. 18, 1991

Related U.S. Application Data

[63] Continuation-in-part of Ser. No. 614,476, Nov. 16, 1990, abandoned.

[51] Int. Cl.$^5$ .............................................. A61B 3/10
[52] U.S. Cl. .................... 351/211; 351/205; 351/206; 351/221
[58] Field of Search ............... 351/203, 205, 206, 211, 351/212, 221

[56] References Cited

U.S. PATENT DOCUMENTS

4,878,750  11/1989  Sekiguchi ........................... 351/205

*Primary Examiner*—Rodney B. Bovernick
*Assistant Examiner*—Hung Xuan Dang
*Attorney, Agent, or Firm*—Townsend and Townsend

[57] ABSTRACT

Badal optics are disclosed in which an aperture array at an optical system under test is interrogated for the deflection of light between a detector array conjugate with the aperture array of the optical system under test being examined. Excursion is measured in a plane normal to the axis of the Badal optics instead of observing towards and away image focus along the axis of the Badal system. In the case of an objective refractor, the eye is illuminated at the retina with a test spot, preferably light in the infrared. An image of a detector array is relayed by a relay lens through the Badal optics to the cornea of the eye, the lens under test. Light emanating from the test spot on the retina passes through the eye lens at the at the image of the detector array. This light undergoes excursion in accordance with the power of eye lens under test at each aperture of the detector array. The extent of this excursion is determined by a moving boundary locus between the image of the detector array and the detector array itself. This excursion is related directly to the eye prescription.

13 Claims, 3 Drawing Sheets

AUTOMATIC REFRACTOR, LENSMETER AND KERATOMETER UTILIZING BADAL OPTICS

This application is a Continuation-in-Part of application Ser. No. 07/614,476 filed Nov. 16, 1990, now abandoned.

This invention relates to Badal optics. More specifically, Badal optics are disclosed where refractive excursion of light between an aperture array imaged at optical system under test and a detector array is utilized to determine the power of the optical system under test. A first embodiment adapts this principle to an objective refractor. A second embodiment adapts the principle to a lens meter. A variation of the lens meter is disclosed in which the Badal optic train is utilized with light converging along an approximated aplanatic path for the contact lenses to avoid the adverse effects of spherical aberration. A third embodiment adapts this principle to keratometers.

BACKGROUND OF THE INVENTION

Badal systems are known and most usually encountered in testing of the human eye. Such a system is illustrated with respect to FIG. 1.

Figure 1:
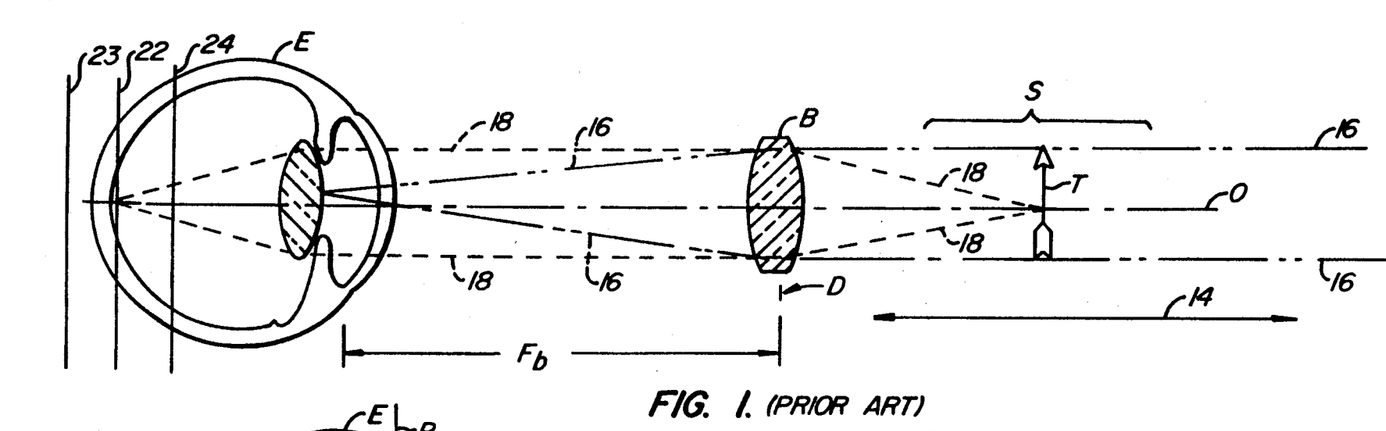
FIG. 1 is a side elevation view of a prior art Badal optometer for subjectively measuring the prescription of a human eye, this prescription being directly related to the distance at which the patient recognizes a target object in the Badal space being in focus.

Referring to FIG. 1, a Badal lens B is placed in front of a human eye E. The Badal lens is positioned so that its focal point is coincident with the position of the eye to be tested. Although only one lens is here illustrated, the reader will understand that more than one lens is more typical of such systems.

The patient at eye E views an acuity target T through the Badal optics B, this target being positioned for towards and away movement 14 with respect to the patient along an optic axis O in what is usually referred to as the Badal space S on the opposite side of the Badal optics from the patient's eye.

The patient subjectively determines when the target T on the opposite side of the Badal lens is in focus. Thereafter the distance D of the object from the Badal optics is determined and related to the power of the patients eye. By relating this determined power of the patient eye to the emmetropic standard, the prescription required for the correction of the patient's vision is determined.

It is a characteristic of the Badal system that the target examined by the patient on the opposite side of the Badal optics does not change size. This phenomena can be understood in the diagram of the line 16. A second, fundamental, property of a Badal system is that the "effective power" generated in the focal plane of the Badal system is linearly related to the movement of the target T in the Badal space.

Specifically, since the Badal lens is one focal length from the eye of the patient, all light from the image of the patients eye is parallel at lines 16 once it passes through the Badal optics to the so-called Badal space on the opposite side of the Badal optics from the patients eye. Thus what the patient sees during the toward and away motion is the Badal object or target T moving into and out of focus—but always maintaining the same dimension.

The distance that the target moves with towards and away movement and comes into focus in the Badal space is a function of the power of the patients eye. Considering the case of light focusing on the eye of the patient at broken lines 18. In FIG. 1, an example is used of an emmetropic eye (the eye having "perfect" vision when the eye is in the "relaxed" state) focused to optical infinity. It can be understood that such focus will occur when the light incident to the eye from the Badal object is parallel. This light will be parallel when the target is at one Badal lens focal length from the emmetropic eye. Thus, for the emmetropic eye, all light from the target to the eye will be parallel—just as all light from the eye to the object will be parallel. For purposes of this analysis, the light can be said to come to focus at the retina along plane 22.

Considering the case of an eye with hypermetropia (farsighted), it will be understood that parallel light seen by the eye (in the so-called "relaxed" state) will focus behind the retina at plane 23. By converging the light seen by the eye, light can be brought into focus at the patient' retina.

In this case, target T is move slightly more than one focal length from the Badal optics B. Parallel light from the target T to the Badal optics B is refracted by the Badal lens to have slight convergence. This slight convergence coupled with the less than optimum convergence of the hypermetropic eye produces focus of the image of the target T on the patient's retina at plane 22.

Considering the case of an eye with myopia (nearsightedness), it will be understood that parallel light seen by the eye (in the so-called "relaxed" state) will focus in front of the retina at plane 24. By diverging the light seen by the eye, light can be brought into focus at the patient's retina at plane 22.

In this case, target T is moved slightly less than one focal length from the Badal optics B. Parallel light from the target T to the Badal optics B is refracted by the Badal lens to have slight divergence. This slight divergence coupled with the more than optimum convergence of the myopic eye produces focus of the image of the target T on the patient's retina at plane 22.

Those having skill in the optic arts will realize that the above explanations are over simplified. Taking the most commonly encountered case of astigmatism, it will be appreciated that the focus of the Badal optics must be broken down into components or "principal meridians". Since the introduction of these complications is fully understood in the art, the following disclosure will continue assuming for the most part focus of the eye in a single principal meridian. The incorporation of additional meridian measurements and their combination to prescribe the astigmatic eye will be for the most part assumed hereafter.

It will be realized from the above descriptions that all Badal systems described have relied upon a Badal object or target T moving with towards and away motion in the Badal space to effect either convergence or divergence for the correction of the other than emmetropic eye. What follows is a Badal system. However, measurement is not made by movement of an object towards and away from Badal optics. Instead, measurement is made by sampling the optical system under test at discrete points and measuring excursion in a plane normal to the axis of the Badal system.

Regarding the keratometer disclosed herein, two types of kerotometric design principles are relevant. These are the Javal design principle and the Helmholtz design principle.

In the Helmholtz design principle, the incident light upon the cornea from an individual source is collimated at a fixed angle. The area sampled on the cornea is moved over the cornea. This movement continues until the light comes off the cornea at a fixed angle. It is this movement of the sample spot on the surface of the eye which is measured to measure the curvature of the eye.

In the Javal keratometer design principle, the incident light upon the cornea is directed to the same spot on the cornea. This light, however, is varied in angle until the sampled and reflected light comes off the cornea at a fixed angle from the fixed sample area on the cornea. The measurement of curvature is found from the position of the source angle.

SUMMARY OF THE INVENTION

Badal optics are disclosed in which an aperture array at an optical system under test system is interrogated for the excursion of light between a detector array conjugate with the aperture array of the optical system under test being examined. Excursion is measured in a plane normal to the axis of the Badal optics instead of observing towards and away image focus of a target along the axis of the Badal system.

In the case of an objective refractor, the eye is illuminated at the retina with a test spot, preferably light in the infrared. An image of a detector array is relayed by a relay lens through the Badal optics to the cornea of the eye, the lens under test. Light emanating from the test spot on the retina passes through the eye lens at the image of the detector array. This light undergoes refractive excursion in accordance with the power of eye lens under test at each aperture of the detector array. The extent of this excursion is determined by a moving boundary locus between the image of the detector array and the detector array itself. This excursion is related directly to the eye prescription.

In the case of a lens meter, the lens to be tested is illuminated from one side toward a detector array with either parallel light for conventional lenses or converging light satisfying the aplanatic condition for avoiding spherical aberration in the case of a contact lens. Light emanating from the lens under test is restricted to a the pattern of a detector array, either by a mask at the lens under test or the relay of a detector array to the optical system under test. This light passing through the optical system under test and emanating from the optical system under test at the individual aperatures of the detector array undergoes excursion at each aperture in accordance with the power of the lens under test. The extent of this excursion between the detector array at the optical system under test and the detector array at the detector is determined by a moving boundary locus between the detector array at the optical system under test and the detector. This excursion is related directly to lens power.

Provision is made in the case of the lens meter for the examination of contact lenses to provide a second light source for incidence to the contact lens along the aplanatic light path to approximate out deviations in the prescription due to spherical aberration on out of the eye contact lenses.

In the embodiment of the keratometer shown herein, the angular direction of the light impinging on the cornea is fixed. Likewise, the sample point on the eye is fixed and appropriately relayed to a detector array. The detector array functions to measure the direction of light leaving the sampling aperture by measuring the excursion of the light in the Badal optical train as set forth above.

Those skilled in the art will realize that such a keratometer measures the "power" or curvature difference of the surface from a reference "power" which is the curvature of the "mean" cornea (typically one having a 8 mm radius of curvature). As in the case of the lensmeter for contact lenses, an offset power, the above mentioned "mean" power, is added to the measured power to give the final reading of measured curvature. Such a keratometer naturally measures in power or curvature, whereas many keratometers naturally measure in radius of curvature. This presents no problem in practice as one is the reciprocal of the other.

OTHER OBJECTS, FEATURES AND ADVANTAGES

An object of this invention is to disclose a construction of a Badal system in which deflection of light from each aperture of an aperture array at an optical system under test is measured along a plane normal to the axis of the Badal system. These measurements of excursion normal to the optic axis of the Badal system are utilized to create a vector signature of the power of optical system under test. Accordingly, the optical system under test is illuminated for emission of light. Light passes from the optical system under test through a Badal lens and in the direction of a detector array and detector array relay optics in the Badal space. The detector array in the Badal space samples the optical system under test, either by a mask defining sampling apertures mounted at the optical system under test, an array defining the sampling apertues at a detector which are thereafter relayed to the the optical system under test, or both. The Badal lens is mounted with respect to the optical system under test such that the optical system under test is at the focal plane of the Badal lens. Relay optics relay an image of the optical system under test to the detector array, permitting deflection and excursion of the light paths from the sampling apertures at the optical system under test to the detector as a function of the power of the optical system under test.

A system for measuring the excursion of light emitted from the detector aperture sample points between the apertures of the detector array at the optical system under test and the detector array is disclosed, this excursion occurring in a plane that is normal to the axis of the Badal system. The excursion when measured gives a vector signature of lens power, which power may be conveniently converted to components of sphere, cylinder and axis or the equivalents thereof for the measurement of the optical system under test.

An advantage of the disclosed system is that it can be readily adapted to an objective refractor. According to this aspect of the invention, a target light spot, preferably in the infrared, is projected onto the retina of the human eye. The image of a detector with a detector array is relayed onto the pupil plane (or corneal plane) of the human eye, this relay occurring through Badal optics and necessary relay optics. Light from the sample points of the detector array on the eye is transmitted to the detector array along refracted paths which in their refractive excursion can be directly converted to a vector signature of the power of the eye. By relating the eye to an emmetropic standard, prescription can be generated for correction of measured vision defects.

An additional advantage of the disclosed system is that it can be just as readily adapted to a lens meter. According to this aspect, collimated light is passed through the lens under test, preferably at a mask juxtaposed to the optical system under test defining the sampling apertures of the lens. An image of the sampling apertures is passed through the Badal optics and relay optics for incidence on a detector. Between the Badal optics and the relay optics, apparatus for measuring the excursion of light between the sample points on the optical system under test and the detector is placed. Measurement of this excursion can be directly converted to vector signatures directly related to the power of the lens system in sphere, cylinder and axis or their equivalent.

A further advantage of the lens meter utilizing the Badal optics is that it can readily be adapted to the measurement of contact lens removed from the eye. According to this aspect of the invention, the light incident on the contact lens to be measured is given an angle of incidence on the contact lens approximated to the aplanatic condition of the mean spherical curvature of the contact lens. All other measurements taken by the Badal system and following optics remain essentially unchanged. There results a system which readily determines the power of contact lens optics without being appreciably affected by the out of the eye spherical aberration of the contact lens.

Yet an additional advantage of the disclosed system is that it can readily be incorporated into a keratometer. According to this aspect of the invention, light is incident upon an eye under test at a controlled angle and sampled from a known location on the surface of the eye. The image of the sample spot on the eye is relayed to a detector array with the excursion of the light between the sample spot on the eye and the image at the detector array being measured. As before, the amount of this excursion normal to the optical axis between the sample spot on the eye and the relayed image of the sample spot is measured in a Badal type optical train. This is thereafter equated to the curvature of the eye.

BRIEF DESCRIPTION OF THE DRAWINGS

Other objects, features and advantages of this invention will be more apparent after referring to the following specification and attached drawings in which:

FIG. 7B is a view similar to FIG. 7B illustrating the substitution of a lens for the eye shown in FIG. 6; and, FIG. 8 is an embodiment of the keratometer of this invention at the vicinity of the eye only illustrating light incident to an eye along paths incident to the radius of curvature of a "mean" eye having a 4 mm radius of curvature with measured deflection indicating departure from the norm.

DESCRIPTION

In the following discussion, the embodiment setting forth the automatic refractor for the eye will first be discussed. Thereafter the incorporation of the invention set forth into a lens meter will be set forth. With regard to the latter embodiment, an other than trivial adaption will be made to the lens meter for the approximating-out of measured off of the eye contact lens power the effects of spherical aberration.

Automatic Refractor for the Eye

Figure 2:
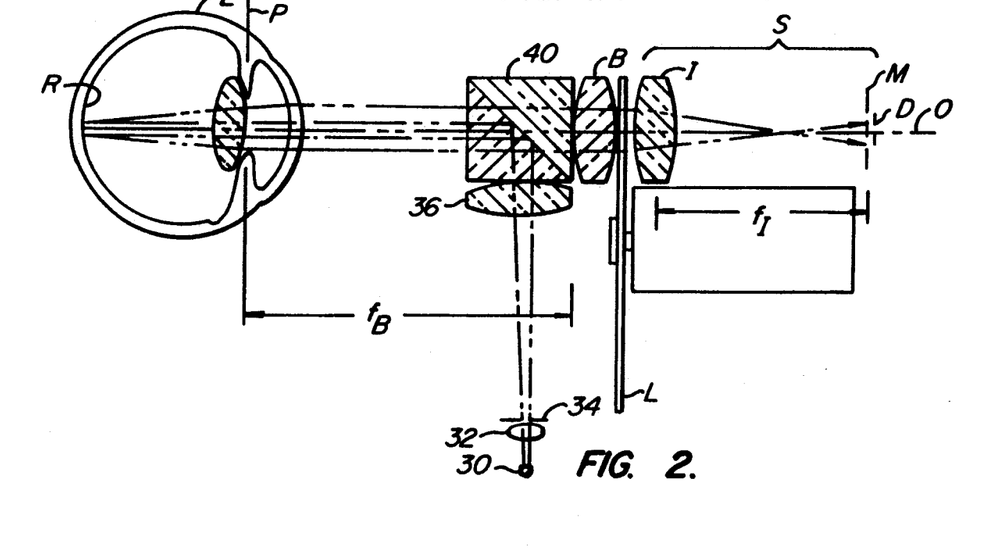
FIG. 2 is a side elevation view of an objective refractor utilizing Badal optics, the apparatus measuring the excursion of light behind the Badal optics in a plane normal to the axis of the Badal system and relating this excursion to vector signature of optical deflection of the eye for determination of objective prescription of the eye.

Referring to FIG. 2, the objective refractor embodiment of the invention herein disclosed is compact and simple in design.

The design is best understood through reference to FIG. 2. Here an eye, E, is shown in cross section looking into the instrument along the optical axis O of the instrument. A source of infrared light 30, most conveniently an LED, illuminates a condensing lens 32 which essentially puts the light into collimation. The beam is then restricted in diameter by the action of aperture 34 which is next placed into its path.

The light next encounters relay lens 36 which is so chosen and placed that it images aperture 34 in the plane of the pupil of the eye P. This beam forming optical system is chosen to insure that light enters the eye through a tightly defined area and that it is well defined beam in angle. Since the beam passes through the refractive portion of the eye in a set, small area, it cannot diverge very much before it reaches the retina even though the refractive properties of eyes examined vary widely.

After passing through lens 36, the beam passes through and is turned 90° by a polarizing beam splitter 40. This type of a beam splitter is used to fold together the illuminating and receiving paths. Additionally, and by virtue of polarizing the light incident on the eye beam splitter 40 suppresses specular reflections from surfaces in the eye and in the common path of the instrument. This suppression occurs because any reflections will have the same polarization as the illuminating beam. Consequently, they will not pass through the polarizing beam splitter to the detector optics. Only light having the opposite polarization can pass into this path. Such reflected light will be harmlessly returned into the source optical path.

The beam next leaves beam splitter 4 and passes into the eye E, illuminating a small, stationary spot on the retina R. This spot serves as a well defined secondary source of light which is used to detect the refractive error of the eye. Although the light incident on this spot is polarized, the diffuse nature of the retinal reflection serves to depolarize the light so that the light emanating from the eye has both polarization components.

The portion of the light reflected from the eye with the correct polarization passes through the beam splitter 40 and into Badal lens B. The focal length of this lens is $f_B$ and the lens is located so that its focal plane P is coincident with the pupil plane of the eye. This lens B can be considered to be the optometer lens of a Badal optometer system whose optometer space S lies on the other side of B from P.

Figure 3:
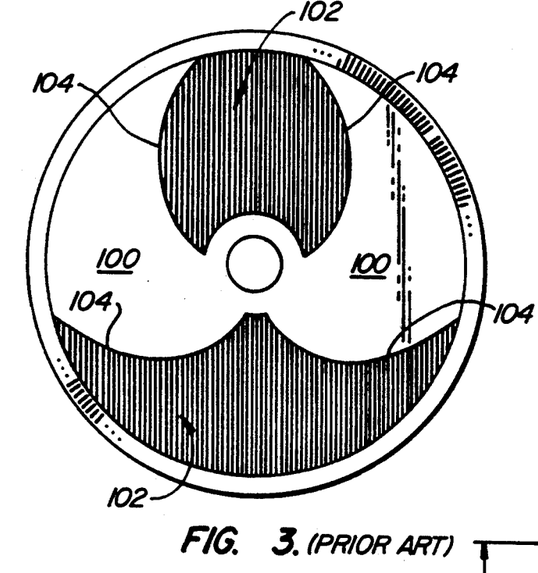
FIG. 3 is a elevation of a prior art moving boundary locus setting forth preferred means for measuring the excursion of light after the Badal optics.

Therefore, the effective lens created by the Badal optometer system lies in the plane of P. On the side of B, which is its optometer space, is a chopper disk or moving boundary locus L. This disk has a portion 100 which is transparent and a portion which is opaque 102. The boundaries 104 between these areas have the characteristic that at any radial distance from the center of the disk, the slope of one boundary must be different than that of the other. In practice a convenient boundary locus is that used in the Humphrey Lens Analyzer. FIG. 3 is an illustration of such a design which is further explained and set forth in U.S. Pat. No. 4,180,325 entitled *Lens Meter With Automated Readout*, issued Dec. 25, 1979, and which is incorporated by reference to this disclosure.

The reader will understand that the moving boundary locus L is only one of a number of device-rotating, linearly moving, or static which can make this measurement. Further, the disk here shown happens to be normal to the optic axis. Other alignments can be used so long as the component of excursion normal to the optic axis can be ascertained.

It will be understood that for measurement of the power of the human eye, it is not practical to place an aperture mask on the human eye. However, by relaying the apertures to the human eye, the same effect is achieved. That is, the apparent or relayed apertures act precisely as if real aperture were substituted in their stead.

After passing the plane of the moving boundary locus L, the light enters imaging lens I, which, in conjunction with lens B, images the pupil of the eye P on multiple aperture M having at least three but typically four or a multiple of four small apertures, arranged in a fixed pattern, most conveniently a square. To do this, multiple aperture M is set at one focal length of lenses B and I, $f_I$, from I.

Directly behind multiple aperture M is a multiple detector D with one discrete element for each aperture on multiple aperture M and arranged so that only light through its assigned aperture can be detected by it. For instance, if there are four apertures in multiple aperture M, then detector D is a quad detector. Furthermore, since the pupil plane P is imaged onto multiple aperture M, multiple aperture M insures that each discrete detector receives light from a tightly defined area of the pupil. Typically these detectors are photo diodes. If the array of photo diodes is made in a sufficiently fixed geometric arrangement and each element is of a controlled small area, then the detector D, itself can serve as a multiple aperture M.

It will now be explained how this arrangement measures refractive error. Because all the rays of light, no matter what the refractive error of the eye under test must pass through the images of the aperture of M created in the plane of P, these image apertures can be considered as sources of the light for lens B and for the Badal system it forms. As this effective source is in the focal plane of Badal lens B, each ray, after passing through Badal lens B must be parallel to all the other members of its bundle.

In addition, because the space on that side of Badal lens B is a Badal optometer space, a ray will intersect the optical axis at a distance from B linearly proportional to the power of the lens under test. Moving boundary locus L is able to measure the distance that a ray is from the optical axis as the ray passes through its plane. Due the fact that all rays are parallel in this space, the distance the ray is from the optical axis in the plane of locus L is proportional to the distance it crosses the optical axis from the Badal lens B and hence it is proportional to the lens power in the plane P, the lens of the eye E.

The signal seen by detector D is similar to the signal seen by the detector in a Humphrey Lens Analyzer and the refractive analysis is done in similar fashion. This may be fully understood by reference to U.S. Pat. No. 4,180,325 entitled *Lens Meter With Automated Readout*, issued Dec. 25, 1979, and which is incorporated by reference to this disclosure.

Automatic Lensmeter with Special Application for Contact Lenses

Figure 4A:
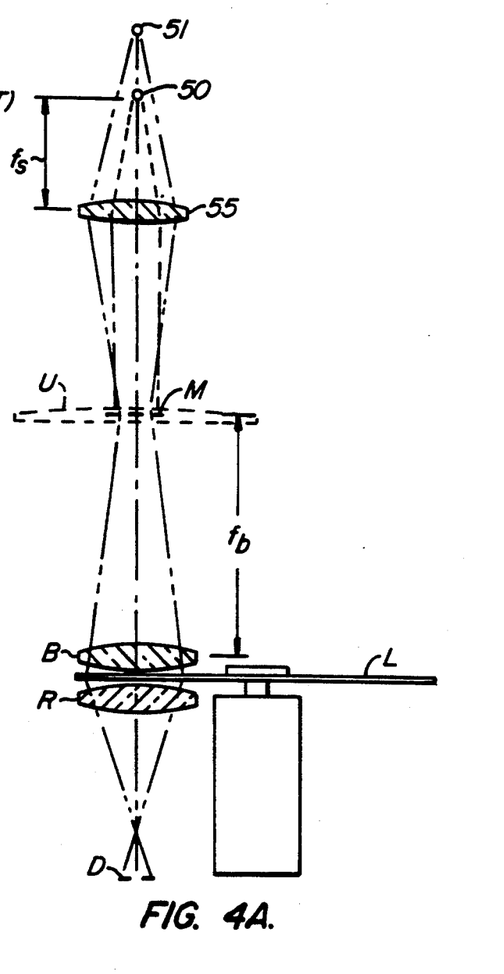
FIG. 4A is a side elevation of a lens meter utilizing Badal optics, the apparatus measuring the excursion of light behind the Badal optics in a plane normal to the axis of the Badal system and relating this excursion to the vector signature of optical deflection of the lens, the system here being shown with a first light source for measurement of conventional spectacle lenses and second light source for aplanatic incidence to contact lenses removed from the eye for minimizing the effects of spherical aberration on measurement of contact lenses; and, FIG. 4B is a detail of the multiple aperture utilized with this invention.

Referring to FIG. 4A, the embodiment of the invention herein disclosed is an automatic lensmeter which is simple in design compared to existing designs and can be constructed in a compact form. It also offers the possibility of measuring contact lens in such a way so as to avoid difficulties with spherical aberration, a fault which interferes with measurements made with existing lensmeters be they manual or automatic.

Figure 4B:
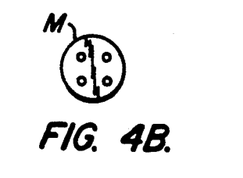

The design is best understood by referring to FIG. 4A. The lens under test U, here shown as a contact lens with negative power, is shown placed with its anterior surface (or vertex adjacent a multiple aperture M. Referring to FIG. 4B, multiple aperture M has at least three but typically four or a multiple of four small apertures arranged in a fixed pattern, most conveniently a square. This multiple aperture M can be a real, physical aperture or it can be the image of a real aperture.

Any light passing through the lens for the purpose of measurement must first pass through one of these apertures of multiple aperture M. Entering the lens on its anterior surface (or vertex) are multiple beams of light, one for each aperture in multiple aperture M. Each of these beams is uniquely defined by the direction of its principal ray which ray is defined as that ray in the bundle which passes through the center of its aperture. After passing through the apertures in multiple apertures M, the light ray bundles next encounter a Badal lens B, which is located such that its focal plane is coincident with multiple apertures M. This Badal lens can be considered to be the optometer lens of a Badal optometer system whose optometer space lies on the other side of Badal lens B from multiple apertures M. Therefore, the effective lens created by the Badal optometer system lies in the plane of multiple apertures M.

On the side of Badal lens B which is its optometer space is a chopper disk or moving boundary locus L. This disk is here illustrated as rotatably driven and has a portion which is transparent and a portion which is opaque. (See FIG. 3.) The boundaries between these areas have the characteristic that at any radial distance from the center of the disk, the slope of one boundary must be different than that of the other. This moving boundary focus has been described in U.S. Pat. 4,180,325, incorporated to this disclosure by reference.

Because all rays of light which pass through the lens under test and reach lens B must pass through one of the apertures in multiple aperture M, these rays form a family of light rays which have an apparent point of emanation from their respective apertures in multiple aperture M. The multiple aperture M acts as an effective source of light. As this effective source of light is in the focal plane of Badal lens B, each ray, after passing through lens B must be parallel to all the other members of its bundle.

In addition, because the space on that side of B is a Badal optometer space, a ray will intersect the optical axis at a distance from B linearly proportional to the power of the lens under test. Moving boundary locus L is able to measure the distance that a ray that passes through its plane is from the optical axis. Due the fact that all rays are parallel in this space, the distance the ray is from the optical axis in the plane of L is proportional to the distance it crosses the optical axis from the Badal lens B and hence it is proportional to the lens power.

Just after moving boundary locus L is another relay lens R, which in conjunction with Badal lens B images multiple aperture M onto detector D. Each area of detector D onto which each aperture of multiple aperture M is mapped is a discrete photo detector. In other words, if there are four apertures in multiple aperture M, then detector D is a quad detector, the preferred manufacture of this invention. Those having skill in the optic arts will understand that at least three such apertures must be provided to obtain lens measurement in sphere, cylinder and axis.

If the areas of detector D are sufficiently discrete and geometrically defined, their image in the plane of multiple aperture M can replace the real apertures. This occurs because of the relay of the detector areas to the plane of multiple aperture M.

Light incident on detector D will create a signal. The signal created by detector D is similar to the signal created by the detector in a Humphrey Lens Analyzer and the refractive analysis is done in similar fashion. Such description is contained in U.S. Pat. No. 4,180,325

The source of light 50 is now discussed. A convenient source is a light emitting diode (LED) which has the benefit of long life and low power requirement. In addition its physical site can be made small. Not only is its overall site small but its light emitting area can be very small which can be used to improve performance as will be shown.

First the source of light for the measurement of spectacle lenses will be discussed. Spectacle lenses U are shown in broken lines. The LED 50 for spectacle lenses is positioned at the back focal point of source or condensing lens 55. Light exiting from condensing lens 55 will therefore be in collimation. However there will be a slight angular divergence of rays in the exiting beam because they come from physically separate areas of the source 50. The maximum divergence of these rays can be expressed as the angle whose tangent is the width of LED 50 divided by the focal length lens 55. This divergence is important in the detection of the transition from light to dark detected by detector D as caused by the action of moving boundary locus L.

The smaller the diameter of the bundle of light in the plane of the locus L, the more rapid the transition and the greater the precision of the measurement. In the absence of a lens under test U, the diameter of the bundle in the plane of the locus L is the diameter of the aperture in M plus the focal length of Badal lens B times the tangent of the angle given above.

When a lens is in place for measurement, this diameter is altered by the action of the lens. This effect is not great because the lens is almost coincident with the aperture M. It is therefore seen that the small site of source 50 gives an advantage to the measurement. It will be seen that the beam exiting lens 55 is a single beam; those having experience in the optical arts will understand that multiple beams enter the lens U under test. The presence of multiple aperture M in effect creates multiple beams for analysis by locus L.

For the measurement of contact lenses, a second source is employed. For this illustration a contact lens under test designated $U_c$ is utilized. This lens $U_c$ occupies the same position as the spectacle lens U previously tested.

As can be seen, source 51 is located on the optic axis O of lens S and on the far side of source 50. It is so placed that a real image of it is created by lens 55 at a distance of 20 mm beyond the plane of multiple apertures M. Therefore in the case of no lens under test, the rays sampled by moving boundary locus L are defined by the apertures in multiple apertures M and the image of light source 51 acting as an effective aperture. This appears in the lensmeter optics, originally calibrated for the spectacle lens source 50, as though a positive lens with a 20 mm focal length (or 50 diopters of power) were under measurement.

When a contact lens is placed adjacent multiple apertures M for measurement, the power of that lens is added to the 50 diopters apparent lens to give a total power measured by the lensmeter. However since it is known to the instrument that it is measuring in the contact lens mode, the 50 diopters is subtracted from the total measurement before the value is displayed. Therefore the displayed value is the true power of the contact lens.

The reason for this unusual arrangement is as follows.

A contact lens, when measured in air with a lensmeter of usual design, wherein a parallel or collimated beams form the measurement beam on one side of the lens, exhibits a large amount of spherical aberration due to its highly meniscus form. This meniscus form is a direct result of the concave surface which on the posterior side allows the contact lens to fit against the surface of the eye.

However, when such a lens is used on the eye, where one side is against the tear film covering the cornea, it forms, in conjunction with the eye, a system which does not exhibit much greater spherical aberration than does the eye without the contact lens. This is because the principal effect of the contact lens is to slightly alter the corneal surface curvature, thereby slightly altering the overall power of the eye so as to correct its refractive error. It must be remembered that the overall power of a human eye is in the neighborhood of 60 diopters, whereas the refractive error is a small fraction of this, lying as it does typically in the range of +5 to −7 diopters. As the effect of the contact lens on the eye creates only a minor change in its optical "form" of the eye system, the spherical aberration (which is a function of "form") of the eye system does not change markedly. Therefore, for the wearer of the contact lens, the paraxial power of the lens represents the effective power.

Due to the spherical aberration exhibited when both sides of the lens are in contact with air, this paraxial power is very difficult to ascertain with a lensmeter of usual design. However if light is brought into the lens with a certain unique vergence condition, there is little if any spherical aberration and a zonal power measurement can be taken as the paraxial measurement.

It is well known in the case of a single refracting surface that the non trivial condition for spherical aberration is satisfied when a converging bundle of rays is brought into the surface in such a way that the converging rays would come to a focus on the same side of the surface as its center of curvature and at a distance D from the lens of:

$$D=(\eta'+\eta)R/N$$

Where
R = radius of curvature of the surface
$\eta'$ = index of refraction on the focus side
$\eta$ = index of refraction on the entry side A first approximation is made that the contact lens acts as the mean curvature of its two surfaces. Thereafter, a second approximation is made that it is sufficient to use a single mean for all contact lens.

Other values in the neighborhood will work. Then if $\eta=1$ and $\eta'=1.5$, L=20 mm. This is the condition satisfied by the above design and gives it the ability to determine paraxial power of a contact lens from a zonal measurement without the confusion of spherical aberration. I hereafter refer to this design as the "aplanatic" condition of the contact lens $U_c$ under test.

Figure 5:
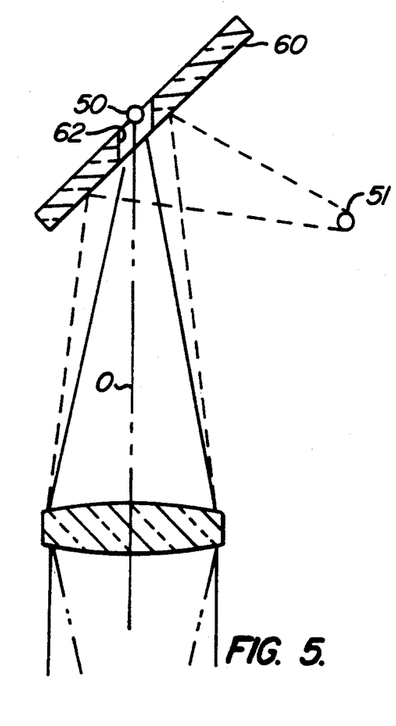
FIG. 5 is a detail of a folded optic path for permitting incidence of light along the axis of the Badal system at two differing distances from the Badal optics, one light source distance permitting conventional spectacle lens measurement and the remaining light source distance for sampling contact lenses at their approximate aplanatic point for minimizing the effects of spherical aberration.

Referring to FIG. 5, a simple folded optical path is shown which can be utilized conveniently for the two light sources. An apertured mirror 60 having central aperture 62 permits light for the conventional or spectacle light source 50 to pass directly on the optic axis O. When measurement of contact lens $U_c$ is desired, source 50 is extinguished and source 51 illuminated. The optical effect is substantially identical to the more understandable—but less practical optical arrangement discussed with respect to FIG. 4.

While the light source arrangement given above is the preferred one, discrete, collimated beams aimed so that they intersect 20 mm or thereabouts downstream of the plane of M can also be used as the contact lens source beams. In like fashion, discrete, parallel beams may be used for the spectacle lens source beams. In practice it may be useful to place masking apertures in the source beams, allowing only the used portions of the total beam to reach the lens U under test.

Keratometer Configuration of Automatic Refractor

It is also possible to reconfigure the above described automatic refractor to act as an automatic keratometer to be used to measure the curvature of the cornea of the eye. This is done by using the same detector apparatus but replacing the light source of the refractor by a multiple or extended keratometer source.

Figure 6:
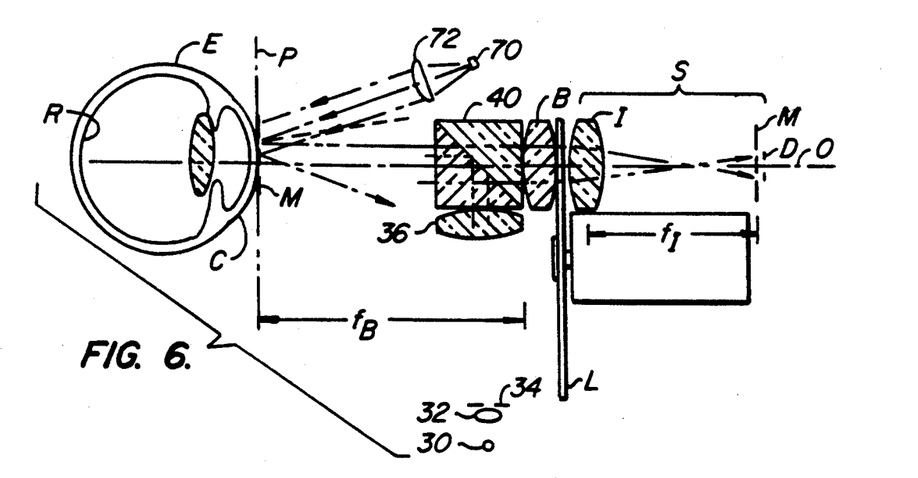
FIG. 6 is a schematic view of a keratometer examining a human eye for curvature at the cornea with a moving boundary locus measure excursion of light in a plane normal to the optical axis of a Badal type optical train.

To develop the rationale for this modification, consider FIG. 6, which is similar to FIG. 2. Source 30 is no longer active. Source 70 and collimating lens 72 have been added which in combination create a collimated beam of light directed at the cornea C of the eye.

The eye E here shown is the typical "normal" eye, having a radius of curvature of 8 mm. Light incident upon such an eye E will be reflected from the sampling points on the eye E at cornea C as parallel rays of light.

Figure 7A:
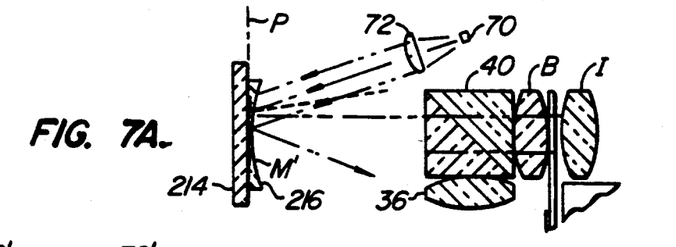
FIG. 7A is a view similar to FIG. 6 at the vicinity of the eye only illustrating the substitution of a mirror and plano-convex lens juxtaposed to the mirror for the eye of FIG. 6.

Referring to FIG. 7A, a convex reflecting surface, such as cornea of the eye, C, may be considered conceptually to be the same as a plane mirror 214 in combination with a negative lens 216. This conceptual transformation of the optical system is shown in FIG. 7A where the cornea C of the eye E has been replaced by the negative lens/plane mirror combination 214, 216. The power of that "lens" is given by the well known formula;

$$P=2/r$$

Where: r = radius of curvature

Figure 7B:
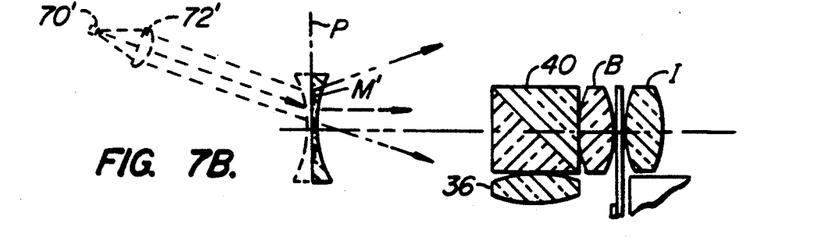

For the purposes of optical analysis it is always possible to "unfold" an optical train at a plane mirror. This second transformation of the optical system is shown in FIG. 7B with the images of the source and its lens labeled 70' and 72'.

It is important to note that the optical system shown here is very similar to the optical system shown in FIG. 4a when source 51 is active. It can be seen that in FIG. 7B, just as in FIG. 4A, the rays of light at an angle to the optical axis strike the optical element under test, passing through fixed apertures in mask M. It is important to note in FIG. 7B, that the apertures from plate M are projected from the detector onto the cornea C. Thus, the place apertures in M of FIG. 4A are taken by the images M' of the apertures of mask M formed by the optical system B, I in plane P.

This similarity suggests that the "power" of the surface can be found using the same algorithms used to find the power of a contact lens with this invention. The difference between the two cases is that in the instance of the contact lens, the incident light was directed at the "aplantatic" point of the lens. In the instance of the corneas, the incident light is directed so that the central ray passing through the sample area on the cornea passes also through the focal point of a cornea whose curvature is in the middle of the human distribution range, ie., approximately 4 millimeters behind the cornea.

In the embodiment of the keratometer shown herein, the angular direction of the light impinging on the cornea is fixed. Those skilled in the art will realized that such a keratometer measures the "power" or curvature difference of the surface from this reference "power" which is the curvature of the "mean" cornea. As in the case of the lensmeter for contact lenses, an offset power, the above mentioned "mean" power, is added to the measured power to give the final reading of measured curvature. Such a keratometer naturally measures in power or curvature, whereas many keratometers naturally measure in radius of curvature. This presents no problem in practice as one is the reciprocal of the other.

One source corresponding to one area of the detector imaged on the cornea as shown by source 70 is not sufficient to make a complete measurement. However as is taught in U.S. Pat. No. 4,407,572, "Keratometer", W. E. Humphrey, three such sources are sufficient. For the modification of an automatic retractor of this invention these three sources are identical to that shown for source 70 and are arranged symmetrically so as to correspond to each of at least three of the segments of the detector. More sources can be used if desired thereby giving redundancy to the measurements.

To show the novelty of this keratometer design principle is contrasted to two well known manual keratometer design principles, the Helmholtz keratometer design principle and the Javal keratometer design principle.

In the Helmholtz design principle, the incident light upon the cornea from an individual source is collimated at a fixed angle. The area sampled is moved on the cornea until the light comes off the cornea at a fixed angle. It is this movement which is measured to measure the curvature.

In the Javal keratometer design principle, the incident light upon the cornea is varied in angle until the sampled light comes off the cornea at a fixed angle from a fixed sample area on the cornea. The measurement of curvature is found from the position of the source angle.

It will be realized that the principle of this invention is a combination of parts of both keratometer design principles. The angle of light upon the cornea is fixed as in the case of the Helmholtz principle. The area of the cornea is fixed in space on the cornea C as in the Javal principle. However the angle of the light coming off the cornea varies in accordance with the curvature of the cornea and this deflection is measured to find the curvature.

It can be understood that this invention can be said to use a third keratometric principle from those already known.

Those having skill in the art will realize that it is possible to use a ring light source, collimated in one dimension to practice this invention. Such ring sources are well known and can be understood when contrasted to a point source of light collimated in one dimension by a cylindrical lens. Such a point source of line after projection through the cylindrical lens will project as a straight line.

Where a source of light disposed in a ring is projected using this cylindrical lens principle, the light source projected is also a ring.

It will be realized in this latter case, the deflection information is only available in a direction (or dimension) perpendicular to the ring. Where deflections occur tangent to the ring, the deflection information is not available (as it is not possible to distinguish one portion of the light source ring from another portion of the light source ring). Therefore, more sample "points" are needed at the cornea. Typically, a reflection of the ring requires double the number of minimum detection areas (up to six separate points) to make up for loss of information tangent to the interrogating ring.

Alternately a different type of detector which can measure radial deflection only, such as a CCD camera can be used as a detector to measure deflection. In such a design, the camera views a ring aperture, which ring is a corneal image, at a distance. Deflection in the plane of the cornea is converted to perpendicular motion in the plane of the CCD. Such a design also forms the basis for an automatic retractor so the keratometer and the retractor can again use the same detector system.

Figure 8:
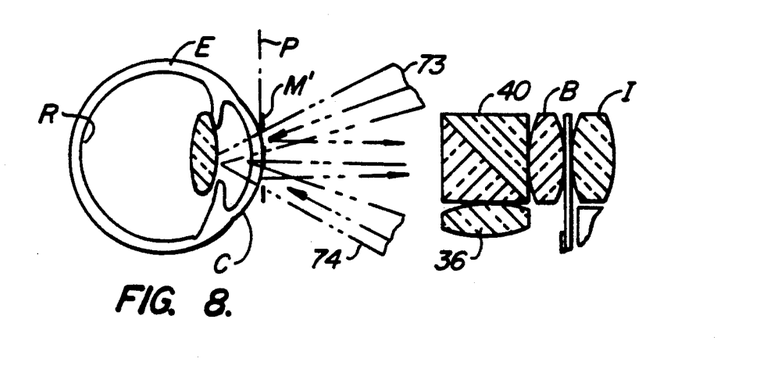

Referring to FIG. 8, it is also possible to use a ring source design which simulates the contact lens source 51 from the lensmeter variation of this invention. The important condition to be met in such a source is that all light rays from the ring shall be so directed that they would pass through the focal point of the "mean" cornea if they were not reflected by the surface of the eye.

This arrangement is shown schematically in FIG. 8. Beam 73 and 74 represent a cross sectional view of the hollow cone of light with its apex at the focal point of the corneal surface. The optical system used to form this beam is not explicitly shown but the formation of such beams are well known to those skilled in the art.

What is claimed is:

1. A Badal system for determining the power of an optical system under test comprising in combination:
    means for emission of light along an optical axis to the system under test;
    a Badal lens positioned along said optical axis having said optical system under test positioned at the approximate focal length of said Badal lens;
    a detector positioned on said optical axis for receiving light passing from said optical system under test and said Badal lens;
    a detector array positioned on said optical axis for forming at said detector at least three sampling apertures for sampling light passing from said optical system under test;
    detector array relay optics between said Badal lens and said detector array for defining a Badal space behind said Badal lens to permit the relay of light from discrete sampling apertures on said optical system under test with the excursion of light between said sampling aperture at said optical system under test and said detector responsive to the deflection of said optical system under test;
    means for measuring the excursion of light emitted between the discrete sampling apertures at the optical system under test and the detector array, this measuring means measuring that displacement normal to the axis of the Badal system whereby the excursion when measured gives a vector signature of power of said optical system under test, which power may be conveniently converted to components of sphere, cylinder and axis or the equivalents thereof for the measurement of the optical system under test.

2. The invention of claim 1 and wherein said optical system under test is the lens of a human eye; and,
    said means for the emission of light along the optical axis comprise means for projecting a target spot of light to the retina of said human eye for emission from said retina through the lens of said eye.

3. The invention of claim 1 and wherein said optical system under test is a lens for the correction of the vision of the human eye; and,
    said means for the emission of light along the optical axis comprises:
    a light source on said optic axis, said light source being positioned on said optic axis with said lens for the correction of the vision of the human eye between said light source and said Badal optics.

4. The invention of claim 3 and wherein said lens for the correction of the vision of the human eye is a contact lens having spherical concave curvature at one surface for disposition on the surface of the human eye; and,
    means coupled to said light source for converging said light passing through said contact lens at an angle approximating the aplanatic refractive condition of contact lens whereby the spherical aberration of said contact lens is reduced in the measurement of said contact lens.

5. The invention of claim 1 and wherein said optical system under test is the cornea of a human eye; and,
said means for the emission of light along the optical axis comprise means for projecting a target spot of light to the cornea of said human eye for reflection from said cornea.

6. A Badal system incorporated to an objective refractor for determining subjectively the power of an eye comprising in combination:
a measuring station for a patient for placing the eye of said patient to an optical axis;
means for emission of light along the optical axis into the human eye;
means for imaging said light at the retina of said eye;
a Badal lens positioned along said optical axis having said human eye at said measuring station positioned at the approximate focal length of said Badal lens;
a detector positioned on said optical axis for receiving light passing light from said image on the retina through said eye and said Badal lens;
a detector array for forming at said detector at least three sampling apertures for sampling light passing through said eye;
detector array relay optics between said Badal lens and said detector array for defining a Badal space behind said Badal lens to permit the relay of light from discrete sampling apertures on said eye with the excursion of light between said sampling aperture at said eye and said detector responsive to the refraction of said eye;
means for measuring the excursion of light emitted between discrete sampling apertures on the eye and the apertures of the detector array, this measuring means measuring that displacement normal to the axis of the Badal system whereby the excursion when measured gives a vector signature of lens power, which power may be conveniently converted to components of sphere, cylinder and axis or the equivalents thereof for the measurement of the eye.

7. The invention of claim 6 and wherein said detector array includes 4 apertures.

8. A Badal system for determining the power of a lens inserted within an optical axis for test comprising in combination:
means for emission of light along said optical axis through said lens from a first side of said lens;
a Badal lens positioned along said optical axis on a second side of said lens, said Badal lens having said lens for test positioned at the approximate focal length of said Badal lens;
a detector positioned on said optical axis at the second side of said lens for test for receiving light passing through said lens for test and said Badal lens;
a detector array positioned on said optical axis for forming at said detector at least three sampling apertures for sampling light passing through said lens for test;
detector array relay optics between said Badal lens and said detector array for defining a Badal space behind said Badal lens to permit the relay of light from discrete sampling apertures on said lens under test with the excursion of light between said sampling aperture at said lens for test and said detector responsive to the refraction at said lens under test;
means for measuring the excursion of light emitted between the discrete sampling apertures at said lens for test and the detector array, this measuring means measuring that displacement normal to the axis of the Badal system whereby the excursion when measured gives a vector signature of lens power, which power may be conveniently converted to components of sphere, cylinder and axis or the equivalents thereof for the measurement of the lens for test.

9. The invention of claim 8 and wherein said means for emission of light to said lens from test emits converging light converging in the range of 20 mm behind said lens for test; and,
said lens for test is a contact lens.

10. The invention of claim 8 and wherein said means for emission of light to said lens for test emits parallel light; and
said lens for test is a spectacle lens.

11. The invention of claim 8 and wherein said means for the emission of light includes first and second light sources, said first light source for emitting parallel light and said second light source for emitting converging light.

12. A Badal system for determining the curvature of an eye under test comprising in combination:
means for emission of light to the cornea of said human eye for reflection from said eye substantially along an optical axis;
a Badal lens positioned along said optical axis having said cornea positioned at the approximate focal length of said Badal lens;
a detector positioned on said optical axis for receiving light reflected from said cornea and said Badal lens;
a detector array positioned on said optical axis for forming at said detector at least three sampling apertures for sampling light reflected from said cornea;
detector array relay optics between said Badal lens and said detector array for defining a Badal space behind said Badal lens to permit the relay of light from discrete sampling apertures on said cornea with the excursion of light between said sampling aperture at said eye under test and said detector responsive to the reflection of said light from said cornea;
means for measuring the excursion of light emitted between the discrete sampling apertures at the eye under test and the detector array, this measuring means measuring that displacement normal to the axis of the Badal system whereby the excursion when measured gives a vector signature of corneal curvature, which curvature may be conveniently converted to components of sphere, cylinder and axis or the equivalents thereof for the measurement of the curvature of said eye.

13. The Badal system of claim 12 and including a collimated light source around said eye causing light to be incident on said eye.

* * * * *